United States Patent [19]

Twigg

[11] Patent Number: 4,777,295

[45] Date of Patent: Oct. 11, 1988

[54] CATALYTIC REDUCTION PROCESS

[75] Inventor: Martyn V. Twigg, Yarm, England

[73] Assignee: Imperial Chemical Industries PLC, London, England

[21] Appl. No.: 887,569

[22] Filed: Jul. 21, 1986

[30] Foreign Application Priority Data

Aug. 1, 1985 [GB] United Kingdom ............... 8519422
Jan. 30, 1986 [GB] United Kingdom ............... 8602329

[51] Int. Cl.$^4$ ............................................. C07C 51/16
[52] U.S. Cl. ..................................... 564/422; 564/421
[58] Field of Search ........................................ 564/422

[56] References Cited

U.S. PATENT DOCUMENTS

| | | | |
|---|---|---|---|
| 2,118,001 | 5/1938 | Andrews et al. | 564/422 X |
| 2,132,389 | 10/1938 | Bertsch | 564/422 |
| 2,822,397 | 2/1958 | Winstrom | 564/422 |
| 3,255,248 | 7/1966 | Suessenguth et al. | 564/422 X |
| 3,544,485 | 12/1970 | Taira et al. | 564/422 X |
| 4,263,225 | 4/1981 | Carter et al. | 564/422 |
| 4,420,648 | 12/1983 | Carter et al. | 564/422 X |
| 4,532,351 | 7/1985 | Barnett et al. | 564/422 X |

*Primary Examiner*—Paul F. Shaver
*Attorney, Agent, or Firm*—Cushman, Darby & Cushman

[57] ABSTRACT

Reduction of aromatic nitro compounds, e.g. nitro-benzene, using a catalyst containing nickel and/or cobalt and at least one difficulty reducible metal oxide, e.g. alumina, particularly alumina plus a rare earth, and having a high nickel/cobalt content.

12 Claims, No Drawings

CATALYTIC REDUCTION PROCESS

This invention relates to a catalytic reduction process and in particular to the catalytic reduction of aromatic nitro compounds to the corresponding amino compounds, e.g. the reduction of nitrobenzene to aniline.

The reduction of aromatic nitro compounds is conveniently conducted by passing a hydrogen containing gas stream into the liquid nitro compound, or into a solution of the nitro compound in a suitable solvent, in which a catalyst is suspended. In a preferred process the amino product is removed from the reaction mixture by distillation.

The catalysts generally employed are usually a finely divided form of nickel, usually supported on an inert oxidic material such as kieselguhr. Such catalysts may be made by impregnation of the support with a heat decomposable nickel salt, e.g. the nitrate, calcination to convert the nickel salt to nickel oxide, followed by reduction of the nickel oxide to active metal with a hydrogen containing gas stream. Alternatively the nickel can be precipitated as hydroxide or carbonate on to the support. The product is then calcined to decompose the hydroxide or carbonate to nickel oxide. In a typical commercial catalyst precursors made by this route, the nickel atoms represent up to about 60% of the total number of atoms (other than oxygen atoms) in the precursor catalyst.

It has been proposed in GB-A-No. 1342020 to employ, for nitrobenzene reduction, a nickel catalyst made by reduction of a precursor pelleted from calcined precipitated crystals of the formula

$Ni_6Al_{1.9}Cr_{0.1}CO_3.(OH)_{16}4H_2O$

In such a catalyst the active metal, i.e. nickel, atoms thus form about 75% of the total number of metal atoms in the catalyst.

We have found that certain catalysts having a higher active metal content are particularly useful.

Accordingly the present invention provides a process process for the production of aromatic amino compounds comprising reducing the corresponding aromatic nitro compound with a hydrogen containing gas stream in the presence of a catalyst containing at least one metal of Group VIII of the perodic table selected from cobalt and nickel intimately associated with at least one difficultly reducible metal oxide, the Group VIII metal atoms constituting 80–98% of total number of atoms, other than oxygen and carbon (if any) atoms in said catalyst.

The aromatic nitro compound is preferably mononuclear and preferably has a single nitro substituent, e.g. as in nitrobenzene. The aromatic nucleus may have other substituents, e.g. alkyl groups such as methyl groups as in the nitrotoluenes.

While the catalysts can be employed as a fixed bed of e.g. pellets, preferably they are employed in a finely divided form suspended in a liquid phase comprising the nitro compound and optionally a solvent therefor, which in many cases is suitably the amino reduction product of the nitro compound. The reaction is preferably conducted by passing a hydrogen containing gas stream, e.g. hydrogen, or hydrogen and an inert diluent e.g. nitrogen, into the liquid phase, preferably with vigorous agitation, with the liquid phase maintained at such a temperature that the product is distilled off from the mixture. It is preferred that the nitro compound is added continuously to the reaction mixture and the product distilled therefrom at a rate corresponding to its rate of formation.

If such a distillation process is adopted for removal of the amino product, the reaction temperature will be governed by the boiling point of the product and the applied pressure. The pressure is preferably such that the reaction temperature is within the range 100° to 250°, particularly 140° to 200° C. By using such a distillation process, the heat of reaction can be employed, at least in part, to supply the heat of vapourisation of the amino product.

In the present invention the catalyst comprises at least one Group VIII metal selected from cobalt and nickel associated with at least one difficultly reducible metal oxide. Where the Group VIII metal is nickel the catalysts have high activity and good selectivity. Where the Group VIII metal is cobalt the activity may not be so high but the selectivity is even better. By using a mixture of cobalt and nickel, particularly mixtures in which the Ni:Co atomic ratio is in the range 0.5 to 5, a useful compromise of high activity and very good selectivity may be achieved. The catalysts have a relatively high Group VIII metal content: thus the Group VIII metal forms 80–98, preferably 85–95, % of the total number of atoms, other than oxygen and carbon (if any) atoms, (i.e. the Group VIII metal atoms plus the metal atoms of the difficulty reducible metal oxide) in the catalyst.

The difficultly reducible oxide can be any oxide of a metal from an A sub-Group (other than Group IA) of the Periodic Table. Preferably it is from Group III A (including rare earths, thoria, and urania) or from Group IV A. Preferably two or more such oxides are present, especially combinations of oxides of aluminium and one or more rare earths, particularly lanthanum and/or cerium: the so-called technical grades comprising a mixture of rare earths may be employed.

The catalyst should be essentially free of other metals or oxides although small amounts thereof may in fact be present as impurities.

The intimate association of the active metal, i.e. the Group VIII metal, and the difficultly reducible oxide can be the result of precipitation, as, for example, hydroxides and/or carbonates, or of applying a solution of a compound of the active metal to a highly absorptive (surface area over 50, especially over 100, $m^2.g^{-1}$) form of the oxide, followed by reduction of the Group VIII metal compound to metal and, if necessary, decomposition of the A sub-Group metal compound to the difficultly reducible oxide.

The catalysts are preferably obtained by sequential, or particularly by simultaneous, precipitation as hydroxides and/or carbonates followed by calcination to decompose the A sub-Group metal compound to the oxide and then, a further reduction to convert the Group VIII metal compound to active metal.

While the reduction to active metal, which is normally effected by heating the catalyst precursor in a hydrogen containing gas stream, can in some cases be effected in the nitro compound reduction reaction vessel, e.g. by suspending the calcined precursor in the heated liquid nitro compound, or solution thereof in e.g. the reduction product, or in an inert liquid or the reduction product of the nitro compound, and passing a hydrogen containing gas stream therethrough, it is preferred to effect reduction of the precursor to active metal off-line. In particular it has been found that the activity of the catalyst tends to increase as the temperature employed for the reduction of the precursor to active metal increases and that the optimum activity is obtained when the reduction to active metal is effected at temperatures considerably higher than those normally encountered during the nitro compound reduction process. Preferably the catalyst precursor is reduced to active metal at a temperature in the range 300°-750°, particularly 350°-700° C. To aid handling of the catalyst precursor before, during, and after reduction to active metal, it may be desirable to form the precursor into a pellet form prior to reduction to active metal. Where the precursor is made by a precipitation route, the precipitated mixture is preferably pelleted after calcination to decompose the precipitate to oxides. However pelleting may be facilitated if calcination prior to pelletting is incomplete so that the calcined mixture contains hydroxides and/or carbonates. Further heating of the pellets to complete the decomposition to oxides may be effected before or during reduction of the Group VIII metal compound to active metal. It is preferred to effect such further heating prior to reduction since it has been found that otherwise methanation of the carbon dioxide released occurs during reduction giving rise to a significant exotherm thereby rendering reduction temperature control difficult.

The reduced catalyst may be stabilised, to aid handling prior to use, by treatment with an inert gas stream containing a small proportion of oxygen during cooling from the reduction temperature. Where such pelletted, stabilised, catalysts are to be used in the form of a suspension of the catalyst, they may be crushed or ground in an inert medium to fine particles prior to use.

The surface area of the active metal in the reduced catalyst is preferably at least 30 $m^2.g^{-1}$ of catalyst.

One particular advantage that has been found by the use of the catalysts having the high Group VIII metal content is that the selectivity of the nitro compound reduction reaction is significantly improved. Thus in the reduction of nitrobenzene to aniline some phenol is produced, probably as a result of hydrolysis of some of the aniline product by water produced in the nitrobenzene reduction. Also some phenyl cyclohexylamine is produced as a result of hydrogenation and condensation reactions: compared to catalysts commonly employed for nitro compound reductions, the high Group VIII metal content catalysts give significantly reduced proportions of such byproducts.

The invention is illustrated by the following examples.

EXAMPLES 1-11

A precipitate was prepared by continuously supplying an aqueous solution, at about 70° C., containing 322 g.l$^{-1}$ nickel nitrate hexahydrate, 23.6 g.l$^{-1}$ aluminium nitrate nonahydrate, and 8.1 g.l$^{-1}$ cerium nitrate hexahydrate to a small precipitation vessel precipitation vessel to which was also supplied an aqueous solution, also at about 70° C., containing 150 g.l$^{-1}$ of sodium carbonate decahydrate, in an amount to maintain the pH in the vessel at about 7. The precipitate was continuously removed from the vessel, filtered hot, washed, and dried for 16 hours at 110° C. The dried precipitate was then calcined for 4 hours at 350 °C. The calcined product had the following composition (after ignition at 900° C.):

| oxide | % by weight |
| --- | --- |
| NiO | 93.1 |
| Al$_2$O$_3$ | 3.7 |
| CeO$_2$ | 3.1 |
| Na$_2$O | 0.1 |

The loss on ignition at 900° C. was 11.3% by weight. The nickel atoms thus formed about 93% of the total number of atoms (other than oxygen atoms) in the calcined catalyst precursor. The calcined product had the following micromeritic properties:

| | |
| --- | --- |
| BET (nitrogen) surface area | 213 $m^2/g^{-1}$ |
| helium density | 5.07 $g \cdot cm^3$ |
| mercury density | 2.44 $g \cdot cm^3$ |
| pore volume | 0.21 $m^2 \cdot g^{-1}$ |

The calcined product was mixed with 1.5% of its weight of graphite and compressed into cylindrical pellets of 3.7 mm diameter and 3.3 mm height.

A 3 cm deep bed of the pellets, supported by fused alumina chips, was charged to a laboratory reactor of 2.5 cm bore. The reactor was heated to the desired reduction temperature and a stream of a mixture of equal volumes of hydrogen and nitrogen was passed through the bed at a rate of 100 l.hr$^{-1}$ (at NTP) for 18 hours.

The nitrogen/hydrogen gas stream was then replaced by a nitrogen gas stream, at a rate of 200 l hr$^{-1}$ (at NTP), while the reactor was cooled to about 100° C. After 1 hour at 100° C., 0.5% by volume of air was bled into the nitrogen stream for 2 hours. The concentration of air in the gas stream was then doubled every 30 minutes until roughly equal proportions of of air and nitrogen were achieved. The gas flow rate was then reduced to 40 l.hr$^{-1}$ and the reactor cooled to room temperature.

This reduction and stabilisation procedure was repeated on fresh samples of the pellets to obtain a series of catalysts that had been reduced at a number of temperatures within the range 300°-700° C. The nickel surface area of the catalysts were determined by adsorption on crushed samples after re-reduction at 230° C. for 2 hours.

The activity of the catalyst samples was assessed by the following procedure.

2 g of the stabilised pellets were crushed with a pestle and mortar under 50 ml of purified aniline and then the resulting slurry was transferred to a stirred 250 ml flask together with a further 50 ml of aniline. Air was displaced from the flask was heated in an oil bath. The flask contents were maintained at 157° C. Hydrogen was passed through the vigorously stirred mixture for two hours at a rate of 180 l.hr$^{-1}$. Small samples were taken at intervals for analysis of their phenyl cyclohexylamine content by gas chromatography. The flask contents were then cooled to 145° C. and 10 ml nitrobenzene added and the hydrogen flow continued for 2 hours, during which time samples were taken for determination of the residual nitrobenzene content.

In the following table the activities, expressed in terms of g of aniline produced per hour per g of stabilised catalyst employed, are quoted for catalysts that had been reduced at different temperatures and for a standard commercial catalyst believed to be nickel supported on kieselguhr and in which the nickel atoms represent about 60% of the total number of atoms (other than oxygen atoms) in the catalyst. During the series of experiments different batches of nitrobenzene (batches A, B, C) were employed, possibly having different purities, which may be responsible for the variation in activity noticed.

In the case of Example 3 the rate of production of phenyl cyclohexylamine per gram of catalyst was 0.2 g.hr$^{-1}$, i.e. about one tenth of that (1.9-2.1 g.hr$^{-1}$) obtained with the standard catalyst. In the other examples of the invention the rate of production of phenyl cyclohexylamine was no more than other 0.1 g.hr$^{-1}$ per g of catalyst.

| Example | Reduction temperature (°C.) | Nickel surface area (m$^2 \cdot$ g$^{-1}$) | Activity (g of aniline produced per hour per g of stabilised catalyst) | | |
|---|---|---|---|---|---|
| | | | nitrobenzene A | nitrobenzene B | nitrobenzene C |
| 1 | 300 | 75 | 2.5 | — | — |
| 2 | 315 | 61 | 2.5 | — | — |
| 3 | 350 | 81 | 3.1 | — | — |
| 4 | 375 | 88 | 3.6 | — | — |
| 5 | 400 | 64 | 3.8 | — | — |
| 6 | 450 | 61 | 3.9 | — | — |
| 7 | 500 | 60 | — | 2.9 | — |
| 8 | 550 | 68 | — | 3.1 | 2.7 |
| 9 | 600 | 39 | — | — | 2.6 |
| 10 | 650 | 23 | — | — | 3.4 |
| 11 | 700 | 21 | — | — | 2.1 |
| Standard catalyst | — | 56 | 4.4 | 3.2 | — |

EXAMPLE 12

The precipitation produre employed in the previous examples was repeated except that the mixed nitrates solution contained:

65.3 g l$^{-1}$ cobalt (as nitrate)
22.9 g l$^{-1}$ aluminium nitrate nonahydrate
7.9 g l$^{-1}$ cerium nitrate hexahydrate.

The precipitate was filtered, washed, dried, and calcined as in the previous examples except that the drying temperature was 120° C. and the calcination temperature 300° C.

The calcined product had the following composition (after ignition at 900° C.):

| oxide | % by weight |
|---|---|
| CoO | 92.2 |
| Al$_2$O$_3$ | 3.2 |
| CeO$_2$ | 3.8 |
| Na$_2$O | <0.1 |

The loss on ignition at 900° C. was 6.7% by weight. The cobalt atoms thus formed about 93.5% of the total number of atoms (other than oxygen atoms) in the calined catalyst precursor. The calcined product had the following micromeritic properties;

| BET (nitrogen)surface area | 132 m$^2 \cdot$ g$^{-1}$ |
|---|---|
| helium density | 5.07 g $\cdot$ cm$^3$ |
| mercury density | 0.90 g $\cdot$ cm$^3$ |
| pore volume | 0.93 km$^2 \cdot$ g$^{-1}$ |

The calcined product was pelletted, reduced (at a reduction temperature of 450° C.), air stabilised and tested as in the previous examples.

The activity was only 46% of that of the standard catalyst but the phenyl cyclohexylamine production rate was only 0.7% of that of the standard catalyst.

I claim:

1. A process for the production of aromatic amino compounds comprising reducing the corresponding aromatic nitro compound with a hydrogen containing gas stream in the presence of a catalyst containing at least one metal of Group VIII of the Periodic Table selected from cobalt and nickel intimately associated with at least one difficulty reducible metal oxide of metals selected from an A sub-group other than Group IA of the Periodic Table, the Group VIII metal atoms constituting 80 to 98% of the total number of atoms, other than oxygen and carbon (if any) atoms in said catalyst.

2. A process according to claim 1 wherein the difficultly reducible metal oxide comprises alumina.

3. A process for the production of aromatic amino compounds comprising reducing the corresponding aromatic nitro compound with a hydrogen containing gas stream in the presence of a catalyst containing at least one metal of Group VIII of the Periodic Table selected from cobalt and nickel intimately associated with at least one difficulty reducible metal oxide comprising alumina and at least one rare earth, the Group VIII metal atoms constituting 80 to 98% of the total number of atoms, other than oxygen and carbon (if any) atoms in said catalyst.

4. A process according to claim 1 wherein the catalyst contains a mixture of the nickel and cobalt and has a nickel: cobalt atomic ratio in the range 0.5 to 5.

5. A process according to 1 wherein the catalyst is made by reducing, at a temperature in the range 300° to 750° C.,
  nickel, and/or cobalt, oxide,
  in intimate admixture with the difficultly reducible metal oxide, or oxides,
said intimate mixture of oxides being obtained by calcining an intimate mixture of precipitated hydroxides, and-/or carbonates, of,
  nickel, and/or cobalt, and
  the metal, or metals, having the difficultly reducible oxide, or oxides.

6. A process according to claim 1 wherein the catalyst has a metal surface area of at least 30 m$^2$.g$^{-1}$.

7. A process according to claims 1 wherein the reduction of the aromatic nitro compound is effected bycontinuously passing a stream of a hydrogen containing gas into a liquid phase comprising the nitro compound in which the catalyst is suspended in finely divided form.

8. A process according to claim 7 wherein the reduction of the aromatic nitro compound is effected by adding the aromatic nitro compound to the reaction mixture and distilling off the product amino compound at a rate corresponding to its rate of formation.

9. A process according to claim 1 wherein the reduction of the aromatic nitro compound is effected at a temperature in the range 100° to 250° C.

10. A process according to claim 1 wherein the difficulty reducible metal oxide is selected from Group IIIA and Group IVA metals.

11. A process for the production of aromatic amino compounds comprising reducing the corresponding aromatic nitro compound with a hydrogen-containing gas stream by continuously passing a stream of a hydrogen-containing gas into a liquid phase comprising the nitro compound in which a catalyst is suspended in finely divided form, said catalyst containing at least one metal of Group VIII of the Periodic Table selected from cobalt and nickel intimately associated with alumina and at least one rare earth oxide, the Group VIII metal atoms constituting 80 to 98% of the total number of atoms, other than oxygen and carbon (if any) atoms in said catalyst.

12. A process according to claim 11 wherein the catalyst is made by reducing, at a temperature in the range 300° to 750° C., an intimate mixture of oxides obtained by calcining an intimate mixture of precipitated hydroxides, and/or carbonates, of
(a) nickel, and/or cobalt,
(b) aluminum, and
(c) at least one rare earth.

* * * * *